(12) United States Patent
Wallace et al.

(10) Patent No.: US 6,544,163 B2
(45) Date of Patent: *Apr. 8, 2003

(54) APPARATUS AND METHOD FOR CONTROLLING A MAGNETICALLY CONTROLLABLE EMBOLIC IN THE EMBOLIZATION OF AN ANEURYSM

(75) Inventors: Michael P. Wallace, Fremont, CA (US); Joseph C. Eder, Los Altos Hills, CA (US); Clifford Teoh, Los Altos, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 256 days.

This patent is subject to a terminal disclaimer.

(21) Appl. No.: 09/752,748

(22) Filed: Dec. 28, 2000

(65) Prior Publication Data

US 2002/0087177 A1 Jul. 4, 2002

(51) Int. Cl.⁷ .......................... A61M 37/00; A61N 2/00
(52) U.S. Cl. .......................................... 600/12; 600/435
(58) Field of Search .................. 600/9, 11, 12, 600/13, 433, 435; 604/93.01, 95.03, 264, 523

(56) References Cited

U.S. PATENT DOCUMENTS

| | | | | |
|---|---|---|---|---|
| 5,108,359 A | * | 4/1992 | Granov et al. | 128/898 |
| 5,122,136 A | * | 6/1992 | Guglielmi et al. | 600/585 |
| 5,236,410 A | * | 8/1993 | Granov et al. | 128/898 |
| 5,250,071 A | | 10/1993 | Palermo | |
| 5,855,578 A | * | 1/1999 | Guglielmi et al. | 606/108 |
| 6,010,498 A | * | 1/2000 | Guglielmi | 606/108 |
| 6,014,580 A | | 1/2000 | Blume et al. | |
| 6,123,714 A | | 9/2000 | Gia et al. | |
| 6,296,622 B1 | * | 10/2001 | Kurz et al. | 604/93.01 |
| 6,315,709 B1 | * | 11/2001 | Garibaldi et al. | 600/12 |
| 6,364,823 B1 | * | 4/2002 | Garibaldi et al. | 600/12 |
| 6,375,606 B1 | * | 4/2002 | Garibaldi et al. | 600/12 |

FOREIGN PATENT DOCUMENTS

| | | |
|---|---|---|
| WO | WO 00 54832 A | 9/2000 |
| WO | WO 00 54835 A | 9/2000 |

* cited by examiner

*Primary Examiner*—Gene Mancene
*Assistant Examiner*—Arnold Castro
(74) *Attorney, Agent, or Firm*—Bingham McCutchen LLP

(57) ABSTRACT

The present invention involves a magnetic embolization apparatus and method for embolizing an aneurysm of a blood vessel. The magnetic embolization apparatus includes a catheter having a distal portion adapted for insertion within an aneurysm of a blood vessel, a permanent magnet carried by the distal portion of the catheter to internally induce a magnetic field from within the aneurysm to control a magnetic field controllable embolic to embolize the aneurysm, and an electromagnet carried by the distal portion of the catheter to internally induce a magnetic field to control delivery of the magnetic field controllable embolic. The method includes delivering a magnetic-field controllable embolic into an aneurysm, inducing a magnetic field in the aneurysm to control the magnetic-field controllable embolic to embolize the aneurysm with the permanent magnet of the catheter, and controlling the delivery of the magnetic-field controllable embolic into the aneurysm with an electromagnet.

19 Claims, 3 Drawing Sheets

APPARATUS AND METHOD FOR CONTROLLING A MAGNETICALLY CONTROLLABLE EMBOLIC IN THE EMBOLIZATION OF AN ANEURYSM

FIELD OF THE INVENTION

The invention relates, in general, to an apparatus and method for forming an occlusion in a mammalian body, and, in particular, to an apparatus and method for controlling a magnetically controllable substance in the embolization of an aneurysm.

BACKGROUND

Like all parts of the body, the brain is composed of living cells that require a blood supply to provide oxygen and nutrients. A hemorrhage in a blood vessel in the brain or in the space closely surrounding the brain is a common cause of strokes. Hemorrhage refers to bleeding into the brain, usually because of a problem with a blood vessel. The problem is often an aneurysm.

An aneurysm is an abnormal bulging outward of blood vessel wall. The wall may smoothly bulge outward in all directions (a fusiform aneurysm) or it may form a sack arising from one wall (a saccular aneurysm). If the aneurysm ruptures, a hemorrhage occurs. This can compress and irritate the surrounding blood vessels, resulting in a reduced supply of oxygen and nutrients to the cells, possibly causing a stroke.

Aneurysms can be treated from outside the blood vessel using surgical techniques or from inside the blood vessel using endovascular techniques. Endovascular treatment of an aneurysm is performed using a catheter. X-ray, magnetic resonance imaging (MRI) equipment, or other visualization equipment may be used to view the progress during the procedure.

A magnetically directable embolic such as an acrylic, iron-containing glue has been proposed to fill or obliterate aneurysms. The embolic is delivered by means of a catheter and is directed into an aneurysm with an external magnetic field generated by a permanent magnet or electrogmanetic device used for Stereotaxis prcedures such as a prototype device made by Steteotaxis Inc. of St. Louis, Mo. An example of such a device is shown and described in U.S. Pat. No. 6,014,580 to Blume, et al. Excess embolic delivered to the aneurysm could enter the bloodstream and cause serious complications downstream, e.g., stroke. The inventors of the present invention have recognized that a need exists to precisely control embolic delivery at the delivery end of the catheter to prevent excess embolic being delivered to the aneurysm.

SUMMARY OF THE INVENTION

An aspect of the present invention involves a magnetic embolization apparatus for embolizing an aneurysm of a blood vessel. The magnetic embolization apparatus includes a catheter having a distal portion adapted for insertion within an aneurysm of a blood vessel, a permanent magnet carried by the distal portion of the catheter to internally induce a magnetic field from within the aneurysm to control a magnetic field controllable embolic to embolize the aneurysm, and an electromagnet carried by the distal portion of the catheter to internally induce a magnetic field to control delivery of the magnetic field controllable embolic.

Implementations of the aspect of the invention described immediately above may include one or more of the following. The permanent magnet is located circumferentially outside or inside the electromagnet. A wall of the catheter includes the permanent magnet. The electromagnet is adapted to induce a magnetic field in a first direction to embolize the aneurysm and in a second direction to counteract the magnetic field of the permanent magnet.

An additional aspect of the invention includes a method of embolizing an aneurysm of a blood vessel. The method includes delivering a magnetic-field controllable embolic into an aneurysm, inducing a magnetic field in the aneurysm to control the magnetic-field controllable embolic to embolize the aneurysm, and controlling delivery of the magnetic-field controllable embolic into the aneurysm by actuating an electromagnet adjacent the aneurysm.

Implementations of the aspect of the invention described immediately above may include one or more of the following. A catheter includes a distal portion with a permanent magnet and the electromagnet located therein, and the permanent magnet is located circumferentially outside the electromagnet and is used to induce the magnetic field in the aneurysm. A catheter includes a distal portion with a permanent magnet and the electromagnet located therein, and the permanent magnet is located circumferentially inside the electromagnet and is used to induce the magnetic field in the aneurysm. A catheter includes a wall with a permanent magnet located therein and the permanent magnet is used to induce the magnetic field in the aneurysm.

The method further includes strengthening the magnetic field induced by the permanent magnet to embolize the aneurysm by actuating the electromagnet, and stopping the delivery of the magnetic-field controllable embolic by reversing polarity in the electromagnet to produce a magnetic field that counteracts the magnetic field of the permanent magnet.

A further aspect of the invention involves a method of embolizing an aneurysm of a blood vessel. The method includes delivering a magnetic-field controllable embolic into an aneurysm with a lumen of a catheter, internally inducing a magnetic field from within the aneurysm to control the magnetic-field controllable embolic to embolize the aneurysm with a permanent magnet of the catheter, and counteracting the magnetic field induced by the permanent magnet with a magnetic field induced by an electromagnet to remove the catheter from the aneurysm without removing the embolic.

Implementations of the aspect of the invention described immediately above may include one or more of the following. The catheter is a dual-lumen catheter having a first lumen and a second lumen, a guide wire is slidably disposed in the first lumen and carries the permanent magnet, the second lumen is adapted to deliver the magnetic field controllable embolic, and the method further includes delivering the magnetic field controllable embolic into the aneurysm through the second lumen and introducing the permanent magnet of the guide wire into the aneurysm to internally induce the magnetic field from within the aneurysm to control the magnetic-field controllable embolic to embolize the aneurysm. The first lumen is defined by a first lumen wall, and the electromagnet is located in the first lumen wall. The catheter is a dual-lumen catheter having a first lumen and a second lumen, the first lumen carries the permanent magnet, the second lumen is adapted to deliver the magnetic field controllable embolic, and the method further includes delivering the magnetic field controllable embolic into the aneurysm through the second lumen.

An additional aspect of the invention involves a magnetic embolization apparatus for embolizing an aneurysm of a blood vessel. The apparatus includes a catheter having a distal portion, a detachable permanent magnetic element and pusher wire carried by the catheter, and an electromagnet carried by the distal portion of the catheter to induce a magnetic field for controlling delivery of the magnetic field controllable embolic.

A further aspect of the invention involves a method of embolizing an aneurysm of a blood vessel. The method includes deploying a detachable permanent magnetic element into the aneurysm; delivering a magnetic-field controllable embolic into the aneurysm so that the detachable permanent magnetic element draws the magnetic-field controllable embolic into the aneurysm to embolize the aneurysm; and controlling delivery of the magnetic-field controllable embolic with an electromagnet.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

DETAILED DESCRIPTION OF THE PREFERRED EMBODIMENTS

Figure 1:
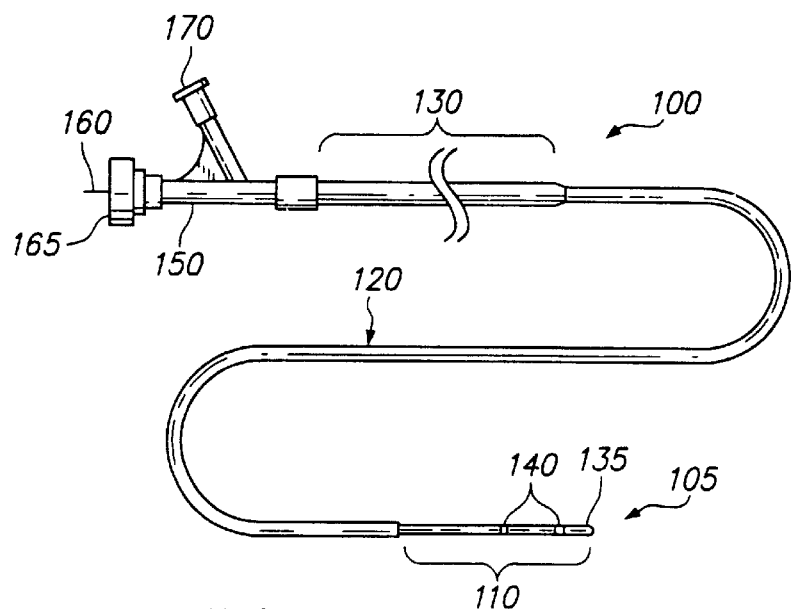
FIG. 1 is a side-elevational view of an embodiment of a catheter that may be used with the magnetic embolization apparatus.

With reference to FIG. 1, an exemplary multi-section catheter 100 that may be used to deliver a magnetic embolization apparatus 105, which is constructed in accordance with an embodiment of the invention, at a targeted aneurysm 107 (FIG. 2) will now be described. The magnetic embolization apparatus 105 induces a magnetic field in the aneurysm 107 to draw and retain a magnetically controllable embolic in the aneurysm 107 and controls delivery of the embolic so that excess embolic is not delivered to the aneurysm 107. Although the invention will be described in terms of aneurysm treatment, it may also be adaptable for endovascular occlusion in arteries, veins, vascular malformations, and arteriovenous fistulas. The invention may also be used for forming an occlusion in other areas of a mammalian body.

The catheter 100 includes a distal section 110, an intermediate section 120, and a proximal section 130. The sections decrease in flexibility from the proximal section 130 to the distal section 110.

The distal section or portion 110 is very flexible and soft to allow deep penetration into the extraordinary convolutions of the neurological vasculature without trauma. The magnetic embolization apparatus 105 is located in the distal section 110 of the catheter 100 at a distal end 135. The distal section 110 may include one or more radio-opaque bands or markers 140 to allow viewing of the position of the distal section under fluoroscopy.

A luer assembly 150 at the proximal section 130 of the catheter 100 accomodates a pusher, core, or guide wire 160. The wire 160 may be made of any well-known guide wire material in the art such as stainless steel. The luer assembly 150 may also include a fluid port 165 for connecting a fluid supply for introducing and/or removing a magnetically controllable embolic and a power port 170 for connecting the catheter 100 to a power supply. The catheter 100 may also include any well-known steering assembly in the art for delivering the magnetic embolization apparatus 105 to the targeted aneurysm 107.

Figure 2:
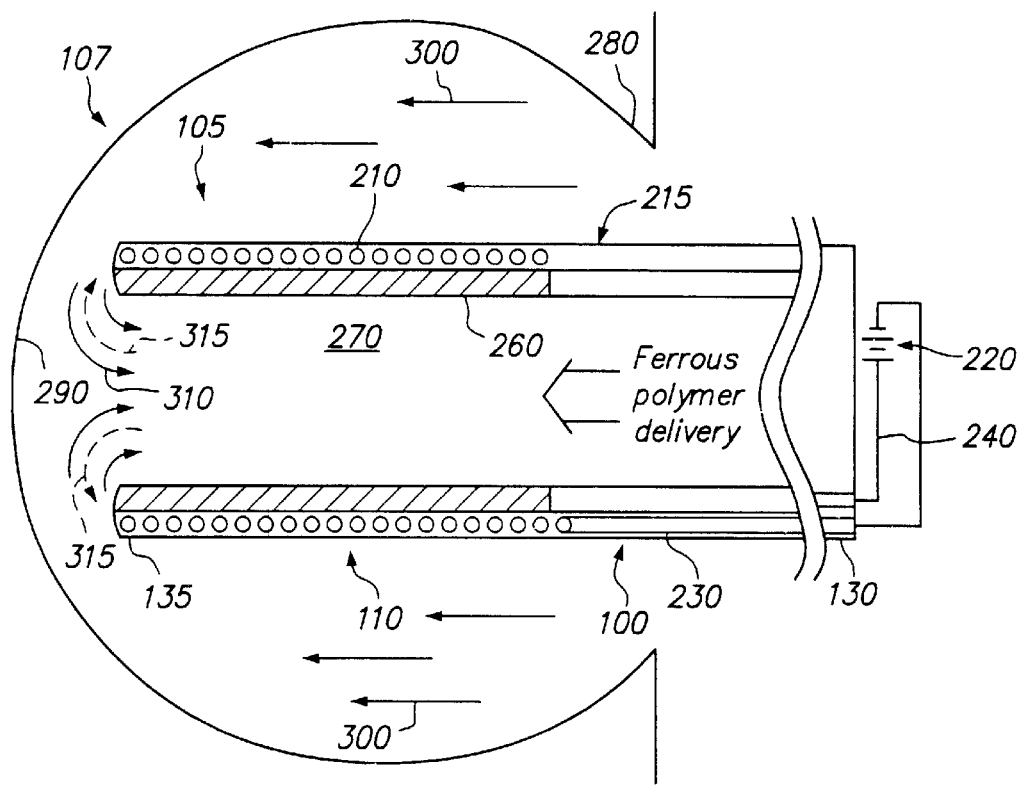
FIG. 2 is a side-elevational view of a distal portion of the catheter illustrated in FIG. 1 in a blood vessel with an embodiment of the magnetic embolizaton apparatus shown disposed in an aneurysm.

With reference to FIG. 2, an embodiment of the magnetic embolization apparatus 105 will now be described. The apparatus 105 includes a coiled solenoid or induction electromagnet 210 located in a wall 215 of the catheter body, in the distal portion 110 of the catheter 100. Electrical current may be supplied to the electromagnet 210 by a power source 220 via a lead wire 230 and returned by a return wire 240 to induce a first magnetic field. Polarity through the electromagnet 210 may be reversed to induce a second magnetic field in an opposite direction from the first magnetic field. A ferrous filling layer or permanent magnet layer 260 may be located in the catheter wall 215, in the distal portion 110 of the catheter 100. The layer 260 may be used to help generate a stronger magnetic field at the end of the catheter 100 and/or help reverse the magnetic field to remove the catheter 100 at the end of the procedure. A lumen 270 defined by an inner portion of the wall 215 delivers a magnetically controllable liquid embolic to the aneurysm 107 and may slidably receive the wire 160 for delivering the catheter 100 to the targeted aneurysm site.

The magnetic embolization apparatus 105 will now be described in use. The catheter 100 is introduced into the vasculature of a patient via a cannula or introducer sheath and snaked through the vasculature of the patient to the targeted aneurysm 107 by any well-known method in the art. X-ray, fluoroscopy or other well-known visualization techniques may be used to assist the physician in directing the catheter 100 to the targeted aneurysm 107. The catheter 100 may be introduced over the guide wire 106 to facilitate delivery of the catheter 100 to the targeted aneurysm 107. The distal end 135 of the catheter 100 may be positioned at the aneurysm site adjacent a neck 280 of the aneurysm 107, at the neck 280 of the aneurysm 107, or within the aneurysm 107. Preferably, the distal end 135 of the catheter 100 is positioned into the aneurysm 107, near a dome 290 of the aneurysm 107.

An external magnetic field 300 may be induced through the aneurysm 107 by an external machine such as a Stereotaxis machine.

Next, a magnetically controllable embolic such as a ferrous polymer (e.g., acrylic, iron-containing glue) that hardens over time is delivered to the aneurysm 107 via the lumen 270 of the catheter 100. In an alternative embodiment, the embolic may have a different composition. The external magnetic field lines 300 cause the iron-containing embolic to fill the aneurysm 107 and be retained within the aneurysm.

Once the aneurysm 107 is filled a sufficient amount, the electromagnet 210 may be actuated, inducing magnetic field lines 310 in generally the opposite direction of the external magnetic field lines 300, to stop further delivery of the ferrous polymer into the aneurysm 107. The electromagnet 210 is actuated by supplying current by the power source 220 through the lead wire 230 to the electromagnet 210. The ferrous filling layer or permanent magnet layer 260 may help in inducing the magnetic field 310 for preventing further delivery of the ferrous polymer to the aneurysm 107. The electromagnet 210 helps to provide precise control of the delivery of the magnetically controllably embolic to the aneurysm 107. The strength of the magnetic field induced by the electromagnet 210 may be controlled by varying the power supplied to the electromagnet 210. It is important that too much embolic does not get delivered to the aneurysm 107 because excess embolic can cause serious complications downstream, e.g., stroke. Controlling embolic shut off with the the electromagnet 210 at the distal portion 110 of the catheter 100 is more precise than controlling shut off at the supply end of the catheter 100 because of the additional volume of the embolic in the catheter lumen 270 that must be accounted for when controlling fluid delivery at the supply end. The electromagnet 210 may also be used to retrieve cured magnetically controllable embolic that may have escaped the aneurysm 107.

After the electromagnet 210 is actuated, the catheter may be withdrawn from the aneurysm 107 and removed from the body. The Stereotaxis machine may be shut off and the external magnetic field 300 terminated after the embolic has hardened or polymerized a sufficient amount.

Alternatively or additionally, the electromagnet 210 and/or ferrous filling layer or permanent magnet layer 260 may be used to help generate a strong magnetic field 315 at the end of the catheter 100 for drawing the embolic into the aneurysm 107. This may be done in addition to or instead of the external magnetic fields 300 generated by the Stereotaxis machine. When the aneurysm 107 has been filled a sufficient amount, the polarity of the electromagnet 210 may be reversed to inhibit further delivery of the embolic.

Figure 3:
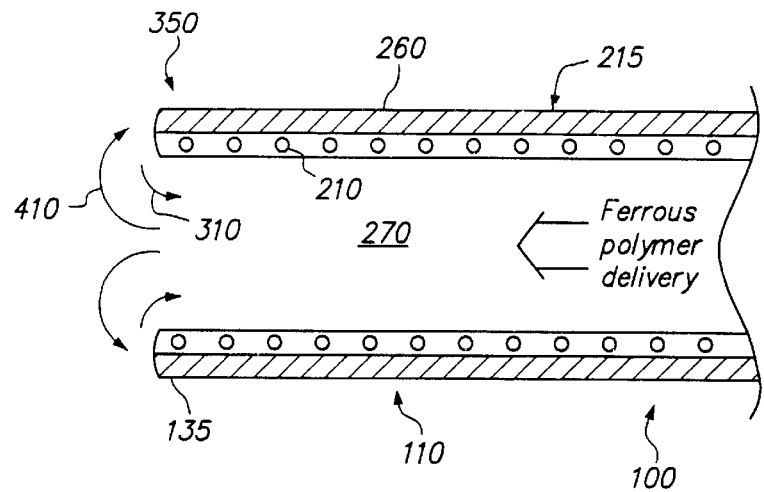
FIG. 3 is a side-elevational view of a distal portion of a catheter with an additional embodiment of a magnetic embolization apparatus shown.

With reference to FIG. 3, a magnetic embolization apparatus 350 constructed in accordance with an additional embodiment of the invention and method of use are the same as that described above with respect to FIG. 2 for the magnetic embolization apparatus 105, except the electromagnet 210 is located circumferentially inside of the ferrous filling layer or permanent magnet layer 260 in the catheter wall 215. Locating the electromagnet 210 circumferentially inside of the ferrous filling layer or permanent magnet layer 260 helps to enable a stronger magnetic field and, thus, higher force in the aneurysm 107 to hold the embolic in place.

Figure 4:
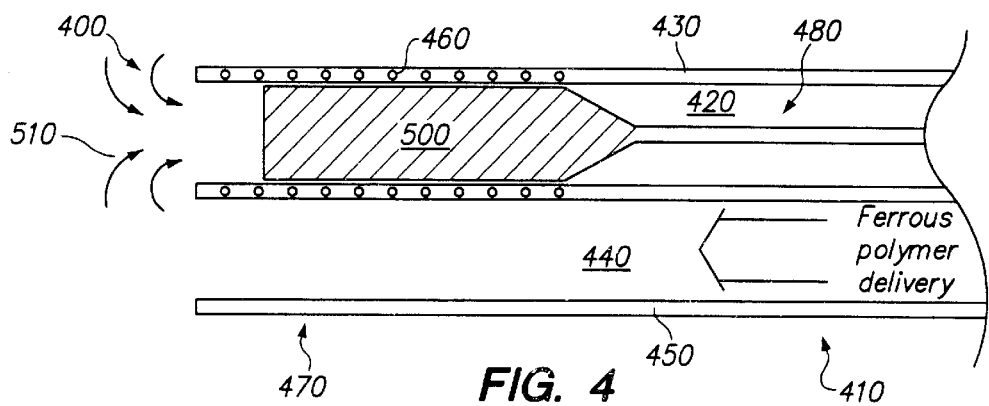
FIG. 4 is a cross-sectional view of a distal portion of a catheter including a further embodiment of a magnetic embolization apparatus shown.

With reference to FIG. 4, a magnetic embolization apparatus 400 constructed in accordance with another embodiment of the invention will now be described. The apparatus 400 is part of a dual-lumen catheter 410 having a first lumen 420 defined by a first lumen wall 430 and a second lumen 440 defined by a second lumen wall 450. The apparatus 400 includes a coiled solenoid or induction electromagnet 460 located in the first lumen wall 430, in a distal portion 470 of the catheter 410. A guide wire 480 may be slidably disposed within the first lumen 420. At least a distal portion 490 of the guide wire 480 includes a ferrous portion or permanent magnet 500. Ferrous polymer is delivered to the aneurysm site through the second lumen 440.

In use, the magnetic embolization apparatus 400 is snaked through the patient's vasculature to the targeted aneurysm site. The ferrous polymer is delivered to the aneurysm 107 through the second lumen 440. Magnetic field lines 510 induced from the ferrous portion or permanent magnet 500 cause the ferrous polymer to be drawn into and retained within the aneurysm 107. The ferrous portion or permanent magnet 500 may be maintained within the distal portion 470 of the catheter 410 or may be deployed from the catheter 410, into the aneurysm 107. To remove the catheter 410 from the aneurysm 107, the solenoid 460 may be actuated to overcome, counteract, or cancel out the magnetic field 510 of the ferrous portion or permanent magnet 500.

In an alternative embodiment, the solenoid 460 may be actuated to create, in conjunction with the magnetic field 510 induced from the ferrous portion or permanent magnet 500, a strong magnetic field for drawing and retaining the ferrous polymer in the aneurysm 107. To remove the catheter 410 from the aneurysm 107, the polarity through the solenoid 460 may be reversed to overcome, counteract, or cancel out the magnetic field of the ferrous portion or permanent magnet 500.

Figure 5:
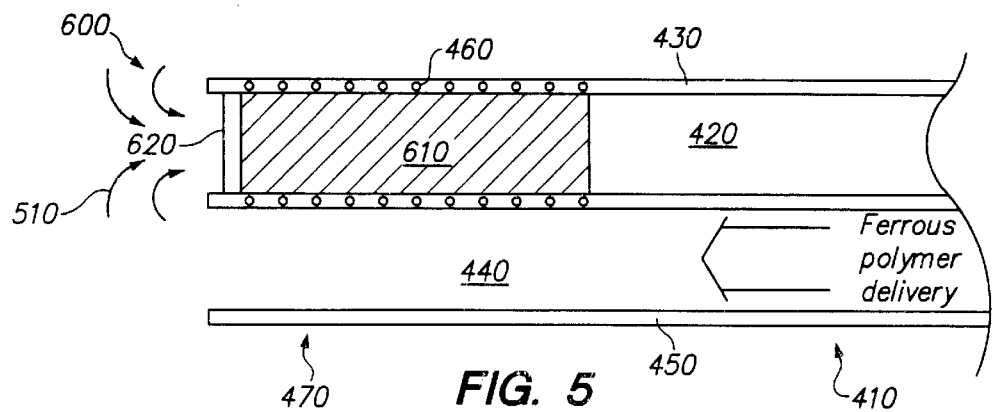
FIG. 5 is a cross-sectional view of a distal portion of a catheter including a still further embodiment of a magnetic embolization apparatus shown.

With reference to FIG. 5, a magnetic embolization apparatus 600 constructed in accordance with a further embodiment of the invention will now be described. The magnetic embolization apparatus 600 is similar to the magnetic embolization apparatus 400 described above, except the guide wire 480 is replaced with a ferrous portion or permanent magnet 610. A plug 620 may be located at a distal end 630 of the first lumen 420 to prevent the ferrous polymer from entering the first lumen 420.

The method of use for the magnetic embolization apparatus 600 is the same as that described above with respect to the magnetic embolization apparatus 400, except the ferrous portion or permanent magnet 610 of the apparatus 600 can not be deployed into the aneurysm 107 apart from the catheter 410.

Figure 6:
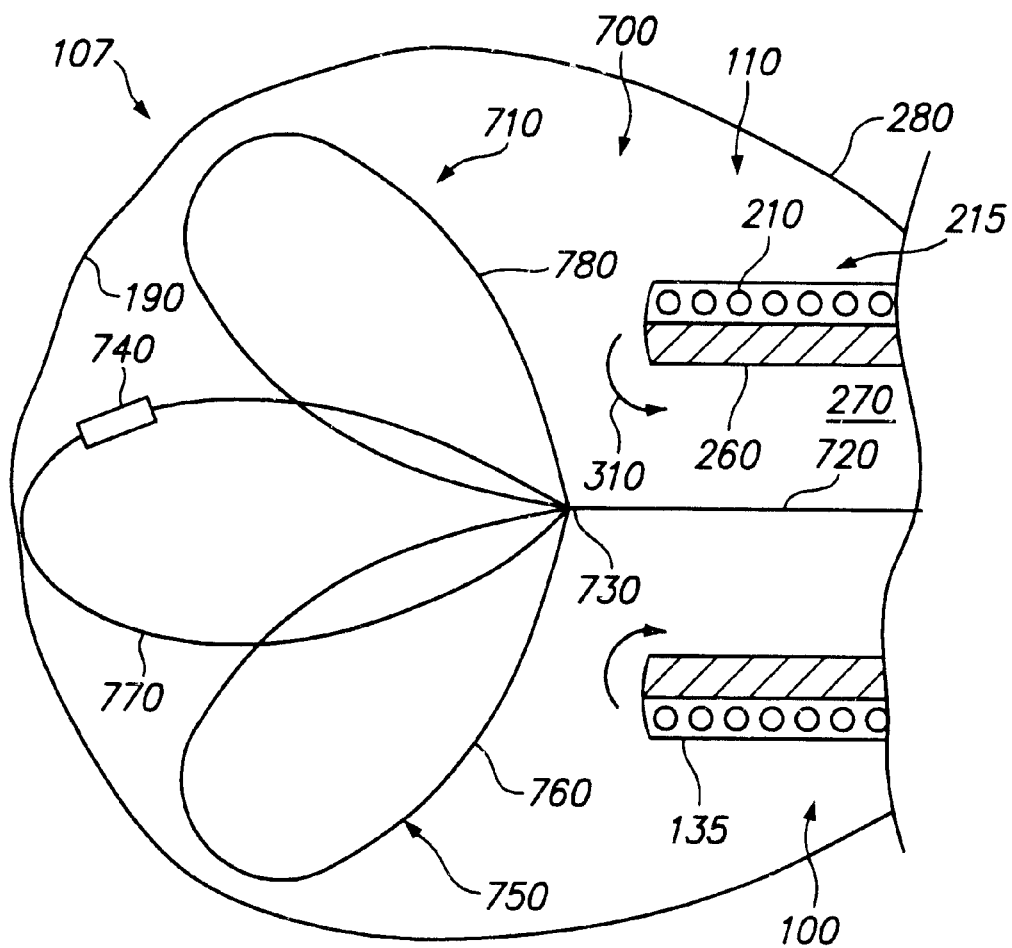
FIG. 6 is a cross-sectional view of a distal portion of a catheter including an additional embodiment of a magnetic embolization apparatus shown disposed in an aneurysm.

With reference to FIG. 6, a magnetic embolization apparatus 700 constructed in accordance with a further embodiment of the invention will now be described. The magnetic embolization apparatus 700 is similar to the magnetic embolization apparatus 105 described above with respect to FIG. 2, except the apparatus 700 also includes a detachable permanent magnetic element 710 detachably connected to a pusher, guide, or core wire 720 by a detachment mechanism 730. The element 710 includes one or more permanent Neodynium (NdFeB) or Samarium Cobalt (SmCo) magnets 740. The element 710 is shaped to retain or secure itself within the aneurysm 107. In the embodiment shown, the element is a multi-loop assembly 750 made of a shape memory material such as Nitinol™. The multi-loop assembly 750 may be a modified TriSpan™ coil sold by Target Therapeutics® of Freemont, Calif. The multi-loop assembly 750 preferably includes three wire wings or loops, a first wire loop 760, a second wire loop 770, and a third wire loop 780. Although the assembly 750 is shown as having three wire loops, other numbers of loops may be used. The expanded wings or loops 760, 770, 780 of the multi-loop assembly 750 help to secure the element 710 in the aneurysm 107 once the assembly 750 is deployed in the aneurysm 107.

The detachment mechanism 730 may be a mechanical detachment mechanism such as that described in U.S. Pat. No. 5,250,071 ("the '71 patent") to Palermo or an electrolytic detachment mechanism such as those described in U.S. Pat. No. 5,122,136 ("the '136 patent") to Guglielmi, et al. and U.S. Pat. No. 6,123,714 ("the '714 patent) to Gia, et al. The '71, '136, and '714 patents are incorporated by reference as though set forth in full. Preferably, an electrolytic detachment mechanism similar to those described in the '136 patent or the '714 patent is used. An electrolytic detachment mechanism includes an electrolytic, sacrificial joint that separates when a small electric current is applied therethrough. The '136 patent describes a soldered electrolytic, sacrificial joint and the '714 patent describes a solderless electrolytic, sacrificial joint.

Although the detachable magnetic element 710 has been described as having a multi-loop configuration, in alternative embodiments, the element 710 may include other configurations. Further, the detachable magnetic element 710 may come in a variety of sizes to accommodate different size aneurysms and/or a variety of configurations to accomodate aneurysms having different shapes.

In use, once the distal end 135 of the catheter 100 is delivered to the aneurysm 107, the detachable permanent magnetic element 710 may be deployed within the aneurysm 107. This may be accomplished by advancing the pusher wire 720 distally through the lumen 270 of the catheter 100. Preferably, the magnetic element 710 has a pre-shaped memory so that the magnetic element 710 will automatically deploy into the configuration shown in FIG. 6 when the magnetic element 710 is advanced into the aneurysm 107. In an alternative embodiment, the catheter 100 may include a sheath that is retracted to deploy the element 710. The wire loops 760, 770, 780 hold the magnetic element 710 securely within the aneurysm 107.

Next, the magnetically controllable embolic is delivered to the aneurysm 107 via the catheter 100. The one or more permanent magnets 740 of the magnetic element 710 internally attracts, from within the aneurysm 107, the magnetically controllable embolic to the magnet(s) 740, filling the aneurysm 107. The magnetic element 710 may be detached from the wire 720 using the detachment mechanism 730 before or after the embolic is delivered to the aneurysm 107. Further, if the magnetic element 710 is detached from the wire 720 after the embolic is delivered to the aneurysm 107, the magnetic element 710 may be detached from the wire 720 after the embolic has sufficiently hardened or polymerized in the aneurysm 107.

Once the aneurysm 107 is filled a sufficient amount, the electromagnet 210 may be actuated, inducing magnetic field lines 310 in the general direction shown in FIG. 6, to stop further delivery of the ferrous polymer into the aneurysm 107. The ferrous filling layer or permanent magnet layer 260 may help in inducing the magnetic field 310 for preventing further delivery of the ferrous polymer to the aneurysm 107. In an alternative embodiment, as illustrated in FIG. 3, the position of the electromagnet 210 and permanent magnet layer 260 may be switched. In a further embodiment, the apparatus 700 may not include a permanent magnet layer 260.

After the electromagnet 210 is actuated, the catheter may be withdrawn from the aneurysm 107 and removed from the body.

Thus, the embodiment of the magnetic embolization apparatus 700 illustrated in FIG. 6 replaces the Stereotaxis machine and the external magnetic field provided therefrom (may also replace the permanent magnet layer 260) with a detachable permanent magnetic element 710 that internally induces, from within the aneurysm 107, a magnetic field to draw the magnetically controllable embolic into the aneurysm for embolization purposes. It should be noted, the detachable permanent magnetic element 710 may also be used with a magnetic embolization apparatus embodiments other than that illustrated in FIG. 6 such as, but not limited to, those illustrated in FIGS. 3–5.

While embodiments and applications of this invention have been shown and described, it would be apparent to those in the field that many more modifications are possible without departing from the inventive concepts herein. The invention, therefore, is not to be restricted except in the spirit of the appended claims.

What is claimed is:

1. A magnetic embolization apparatus for embolizing an aneurysm of a blood vessel, comprising:

a catheter including a distal portion adapted for insertion within an aneurysm of a blood vessel;

a permanent magnet carried by the distal portion of the catheter to internally induce a magnetic field from within the aneurysm to control a magnetic field controllable embolic to embolize the aneurysm; and an electromagnet carried by the distal portion of the catheter to induce a magnetic field that counteracts the magnetic field of the permanent magnet.

2. The apparatus of claim 1, wherein the permanent magnet is located circumferentially outside the electromagnet.

3. The apparatus of claim 1, wherein the permanent magnet is located circumferentially inside the electromagnet.

4. The apparatus of claim 3, wherein the catheter includes a wall with the permanent magnet.

5. The apparatus of claim 3, wherein the catheter is a dual-lumen catheter having a first lumen and a second lumen, a guide wire slidably disposed in the first lumen and carrying the permanent magnet, and the second lumen adapted to deliver the magnetic field controllable embolic.

6. The apparatus of claim 3, wherein the catheter is a dual-lumen catheter having a first lumen and a second lumen, the first lumen carrying the permanent magnet, and the second lumen adapted to deliver the magnetic field controllable embolic.

7. The method of claim 1, wherein the electromagnet is adapted to induce a magnetic field in a first direction to embolize the aneurysm and in a second direction to counteract the magnetic field of the permanent magnet.

8. A method of embolizing an aneurysm of a blood vessel, comprising:

delivering a magnetic-field controllable embolic into an aneurysm;

internally inducing a magnetic field in the aneurysm to control the magnetic-field controllable embolic to embolize the aneurysm;

controlling the delivery of the magnetic-field controllable embolic into the aneurysm by actuating an electromagnet adjacent the aneurysm.

9. The method of claim 8, wherein a catheter includes a distal portion with a permanent magnet and the electromagnet located therein, the permanent magnet is located circumferentially outside the electromagnet and is used to induce the magnetic filed in the aneurysm.

10. The method of claim 8, wherein a catheter includes a distal portion with a permanent magnet and the electromagnet located therein, the permanent magnet is located circumferentially inside the electromagnet and is used to induce the magnetic filed in the aneurysm.

11. The method of claim 8, wherein a catheter includes a wall with a permanent magnet located therein and the permanent magnet is used to induce the magnetic filed in the aneurysm.

12. The method of claim 11, further including strengthening the magnetic field induced by the permanent magnet to embolize the aneurysm by actuating the electromagnet, and stopping the delivery of the magnetic-field controllable embolic by reversing polarity in the electromagnet to produce a magnetic field that counteracts the magnetic field of the permanent magnet.

13. A method of embolizing an aneurysm of a blood vessel, comprising:

delivering a magnetic-field controllable embolic into an aneurysm with a lumen of a catheter;

internally inducing a magnetic field from within the aneurysm to control the magnetic-field controllable embolic to embolize the aneurysm with a permanent magnet of the catheter;

counteracting the magnetic field induced by the permanent magnet with a magnetic field induced by an electromagnet to remove the catheter from the aneurysm without removing the embolic.

14. The method of claim 13, wherein the catheter is a dual-lumen catheter having a first lumen and a second lumen, a guide wire slidably disposed in the first lumen and carrying the permanent magnet, the second lumen adapted to deliver the magnetic field controllable embolic, and the method further including delivering the magnetic field controllable embolic into the aneurysm through the second lumen and introducing the permanent magnet of the guide wire into the aneurysm to internally induce the magnetic field from within the aneurysm to control the magnetic-field controllable embolic to embolize the aneurysm.

15. The method of claim 14, wherein the first lumen is defined by a first lumen wall, the electromagnet located in the first lumen wall.

16. The method of claim 13, wherein the catheter is a dual-lumen catheter having a first lumen and a second lumen, the first lumen carrying the permanent magnet, the second lumen adapted to deliver the magnetic field controllable embolic, and the method further including delivering the magnetic field controllable embolic into the aneurysm through the second lumen.

17. The method of claim 16, wherein the first lumen is defined by a first lumen wall, the electromagnet located in the first lumen wall.

18. A magnetic embolization apparatus for embolizing an aneurysm of a blood vessel, comprising:

a catheter including a distal portion;

a detachable permanent magnetic element and pusher wire carried by the catheter; and an electromagnet carried by the distal portion of the catheter to induce a magnetic field for controlling delivery of the magnetic field controllable embolic.

19. A method of embolizing an aneurysm of a blood vessel, comprising:

deploying a detachable permanent magnetic element into the aneurysm;

delivering a magnetic-field controllable embolic into the aneurysm so that the detachable permanent magnetic element draws the magnetic-field controllable embolic into the aneurysm to embolize the aneurysm;

controlling delivery of the magnetic-field controllable embolic with an electromagnet.

* * * * *